United States Patent [19]
Vona

[11] Patent Number: 5,718,246
[45] Date of Patent: Feb. 17, 1998

[54] PREFERENTIAL INDUCTION OF ELECTRICALLY MEDIATED CELL DEATH FROM APPLIED PULSES

[75] Inventor: Matthew J. Vona, Elk Grove, Calif.

[73] Assignee: Preferential, Inc., Sacramento, Calif.

[21] Appl. No.: 582,509

[22] Filed: Jan. 3, 1996

[51] Int. Cl.$^6$ .................................................. A61N 1/00
[52] U.S. Cl. .................................. 128/898; 600/14; 607/2
[58] Field of Search ......................... 600/10, 14; 607/100, 607/101, 102, 154, 2; 128/898

[56] References Cited

U.S. PATENT DOCUMENTS

| | | |
|---|---|---|
| 4,230,129 | 10/1980 | LeVeen . |
| 4,665,898 | 5/1987 | Costa et al. ........................ 600/14 |
| 4,818,697 | 4/1989 | Liboff et al. ...................... 435/173 |
| 4,850,959 | 7/1989 | Findl ................................ 600/14 |
| 5,010,897 | 4/1991 | LeVeen . |
| 5,045,050 | 9/1991 | Liboff et al. ...................... 600/14 |
| 5,087,336 | 2/1992 | Liboff et al. ...................... 600/14 |

FOREIGN PATENT DOCUMENTS

2370483  7/1978  France .

*Primary Examiner*—William E. Kamm
*Assistant Examiner*—Kennedy J. Schaetzle
*Attorney, Agent, or Firm*—James M. Ritchey

[57] ABSTRACT

A method for inducing necrosis in susceptible malignant cells, comprises two general steps. First, positioning a collection of cells containing the susceptible malignant cells within a treatment domain, wherein the treatment domain is subjected to a non-ionizing radiation field. Second, pulsing said non-ionizing radiation field with a frequency and an intensity selected to produce necrosis in the susceptible malignant cells by creating a transmembrane potential that causes an increase in ionic diffusion in the susceptible malignant cells or generates reversible electroporation of the susceptible malignant cells. Though both malignant and non-malignant cells may be reversibly porated, it is posited that many forms of cancer will be more vulnerable to the subject procedure.

26 Claims, 3 Drawing Sheets

PREFERENTIAL INDUCTION OF ELECTRICALLY MEDIATED CELL DEATH FROM APPLIED PULSES

BACKGROUND OF THE INVENTION

1. Field of the Invention

A method of producing selectively induced (or preferential) necrosis in selected tissues or cells is described. More specifically, the preferential necrosis is generated by employing a low energy electric field that is pulsed to produce a membrane potential of approximately 200 mV (millivolts) to about 700 mV, thereby interfering with normal metabolic pathways via reversible electropotation or increased ionic diffusion.

2. Description of the Background Art

Various methods exist for killing abnormal cells including surgery, chemical treatments, radiation therapy, and others. The radiation techniques include several types of therapy with radioisotopes and high energy ionizing radiation procedures. However, few, if any, reliable radiological methods or combinations of methods exist for eliminating abnormal cells (lymphoma cells and the like) found in close proximity to, or buried within, normal cells without causing significant damage to the normal cells. The subject invention provides a method for eliminating, selectively, malignant or abnormal cells that are intermixed with normal cells.

Radiation treatment methods exist in the prior art. U.S. Pat. No. 4,230,129 discloses a radio frequency electromagnetic radiation device that has an orbital mount. Tumors are treated with radio frequency heating within the body of the animal, including a human.

Related in U.S. Pat. No. 5,010,897 is an apparatus for deep heating of cancers. Two single turn coaxial coils of varying diameter rotate synchronously in planes which are parallel to each other with the central axis of each coil lying in exactly the same line which is perpendicular to the plane of the coil. The summated magnetic field of the rotating coils continuously heats the tumor.

French Patent No. 2370-483 discloses a non-thermal electromagnet treatment process that has a field formed by emission of waves of different orientation. The frequency of emission of the series (each base frequency is from 40 to 80 kHz) is adjusted to be between 4 and 800 Hz.

A pending application (Ser. No. 08/286,671, now U.S. Pat. No. 5,527,352) by the subject inventor describes a non-ionizing radiation emitting apparatus and method of use for preferentially inducing cellular necrosis in abnormal cells. A non-ionizing radiation generator with opposing plates or poles is disclosed. A time focused electromagnetic field with sufficient energy to cause either electroporation or electromagnetic enzyme interference of the abnormal cells is included and functions by rotating the generated radiation about a central axis thereby focusing the radiation at a desired location containing at least a portion of the abnormal cells.

SUMMARY OF THE INVENTION

An object of the present invention is to disclose a method of achieving preferential necrosis of cells by reversible electroporation or induction of transmembrane potential conditions below or equal to those required for reversible electropotation in order to cause alterations in critical metabolic pathways, thereby inducing necrosis in susceptible cells over time.

Another object of the present invention is to present a method for preferential necrosis induction utilizing a pulsed electromagnetic field, whereby a transmembrane potential of about 0.2 V to about 1.5 V or more exactly about 0.2 V to about 0.7 V is induced repeatedly in cells for a sufficient time period to cause necrosis of the abnormal cells resulting from the metabolic alterations induced by electroporation or transmembrane potential dependent phenomenon of each cell's bilayers or by one or more altered ion gradient concentrations.

A further object of the present invention is to supply a method that utilizes pulsed non-ionizing radiation to induce altered ionic diffusion in susceptible or eligible cells, thereby altering metabolic processes which induce necrosis in those susceptible or eligible cells.

Still another object of the present invention is to provide a method that utilizes pulsed non-ionizing radiation to induce an increased ATP consumption rate in susceptible malignant cells, thereby decreasing the ATP available for ion gradient restoration and normal cellular processes, thereby inducing necrosis in those susceptible malignant cells.

Yet a further object of the present invention is to furnish a method that utilizes pulsed non-ionizing radiation to decrease the transmembrane $Na^+$, $K^+$, and $Ca^{2+}$ gradients in susceptible malignant cells, thereby interfering with critical metabolic pathways and producing cellular necrosis in those susceptible malignant cells.

Disclosed is a method for selectively killing susceptible malignant cells by utilizing non-ionizing radiation generating means to produce non-ionizing pulsed radiation. The generated pulsed radiation is at a level sufficient to create cellular transmembrane potentials ($\Delta\Psi M$) of about between about 0.2 V and aboat 1.5 V or more specifically between about 0.5 V and about 0.7 V in the susceptible malignant cells for a selected and sufficient time period to cause necrosis in the abnormal cells via electroporation or increases in ionic diffusion that induce lethal metabolic alterations.

Specifically, disclosed is a method for inducing necrosis in susceptible malignant cells found in either tissue culture or patient. The method comprises positioning a collection of cells, within the above mentioned (or any other suitable) environments, containing the susceptible malignant cells within a treatment domain, wherein the treatment domain is subjected to a non-ionizing radiation field. The non-ionizing radiation field is pulsed with pulses having a pulse duration, interval gap between pulses, and pulse intensity selected to produce necrosis in the susceptible malignant cells by creating a transmembrane potential that causes an increase in ionic diffusion in the susceptible malignant cells or generates reversible electroporation of the susceptible malignant cells. The increased ionic diffusion, reversible electropotation, or other effects triggered by the transmembrane potential mediated event cause a lethal metabolic alteration in the susceptible malignant cells. Usually, the pulse duration, interval gap between pulses, and pulse intensity are selected to produce necrosis in the susceptible malignant cells based on cellular membrane characteristics of the susceptible malignant cells. Generally, the created transmembrane potential is about 0.2 V to about 1.5 V and more specifically about 0.2 V to about 0.7 V.

The subject method may function in susceptible malignant cells via creating a transmembrane potential that causes an increase in ion diffusion in the susceptible malignant cells, thereby causing a lethal metabolic alteration in the susceptible malignant cells over a prederived treatment period. Also, the subject method may function in susceptible malignant cells via creating an increase in ATP requirement in the susceptible malignant cells, thereby causing a lethal metabolic alteration in the susceptible malignant cells. Additionally, the subject method may function in susceptible malignant cells via creating a deleterious alteration in internal pH of the susceptible malignant cells by interfering with normal ion distributions, thereby causing a lethal metabolic alteration in the susceptible malignant cells. It is noted that one or all of the just noted rationales may cause selective necrosis or additional reasons may exits for selective necrosis.

More specifically, disclosed is a method for treating tissue and in particular, a patient having malignant cells, wherein the treatment induces necrosis in the malignant cells that are susceptible to the treatment. The subject method comprises selecting either the tissue or the patient with the malignant cells that are susceptible to the treatment because the susceptible malignant cells produce ATP primarily through glycolytic pathways or the susceptible malignant cells have a variant ion gradient relative to nonsusceptible healthy cells. The patient is positioned to place the susceptible malignant cells within a treatment domain, wherein the treatment domain is subjected to a non-ionizing radiation field. The treatment domain is pulsed with the non-ionizing radiation field. The pulses have a pulse duration, an interval gap between each of the pulses, and pulse intensity selected to produce necrosis in the susceptible malignant cells by creating transmembrane potentials that cause increases in ionic diffusion in the susceptible malignant cells or generate reversible electroporation of the susceptible malignant cells.

Other objects, advantages, and novel features of the present invention will become apparent from the detailed description that follows, when considered in conjunction with the associated drawings.

DESCRIPTION OF THE PREFERRED EMBODIMENT

The subject invention is directed towards the interaction of relatively low energy pulsed electromagnetic fields of generally pulsed non-ionizing radiation with closed cellular systems to produce cellular death. The pulsed non-ionizing radiation of the subject method for preferential necrosis or cancer therapy has fewer harmful side effects than those methods employing higher energy radiations. By utilizing low energy pulsed electromagnetic fields of the subject invention, cellular necrosis can be limited to the transformed cells, without smooth tissue damage and, in general, the commonly observed free radical production produced by exposure to higher radiation.

Cancer cells are often categorized by their degree of malignancy. The degree of malignancy that cells in a particular growth have can correlate to the cells n/c ratio, their propensity to invade surrounding tissues (their invasiveness), the degree of vascularization affiliated with a particular growth, their degree of differentiation, their size (i.e., large cell lymphoma), and many other attributes (Julio H. Garcia, M.D. in *Concepts in Neurosurgery*, 4, Michael Salcman, ed. Williams & Wilkins, Baltimore, 1991, Chapter 2). As the cell's malignancy is increased, pronounced metabolic differences become evident when compared to the metabolic mechanisms found in non-transformed cells due to the fact that the invasive cells are functioning with decreased efficiency by nature of their randomly generated mutations and, hence, variant accuracies of expression. As an example, we will refer to grades III and IV brain glioma.

In illustration, we will compare the more important metabolic consequences of reversible, intermittently applied electroporation (RIAE) or electrically mediated cell death upon grade IV glioblastoma cells and non-transformed glial cells. Though histologically, we have seen that the latter seems to maintain an average internal cell volume below that of the glioma cell (in-vivo) (Philip E. Duffy, Yung-Yu Huang, and Maurice M. Rapport, *Experimental Cell Research*, 139: pp. 145–157, 1982 and Curran and Jones, Tumours Structure and Diagnosis; Harvey Miller, Oxford University Press, 1991)), we shall for the sake of argument assume both cells are roughly identical in this respect. Thus no preferential membrane amplification will be gained by either cell through an increased radius of curvature and membrane separation relative to the field. In the cases that the non-transformed cells have slightly larger average cell volumes, assuming that the electroporation applied is intermittently and reversibly induced, the differences in metabolism of many forms of highly invasive cells will still be less resistive towards RIAE agitation.

The most notable effect that RIAE will have upon the cell is that the transmembrane ion gradients necessary for proper metabolic functioning will be disturbed. If one is able to expedite the transmembrane diffusion of sodium, calcium, and potassium ions (for example), approaching but not reaching fatal rates of transmembrane ionic diffusion, one can effectively up regulate active transport mechanisms for a selected period of time, increasing the energy requirements (here in the form of ATP) of the cell.

The majority of mammalian cells maintain intracellular $Na^+$ concentrations fourteen times lower than the corresponding extra cellular concentrations (Christopher Mathews and K. E. van Holde, "BIOCHEMISTRY", Benjamin/Cummings Pub., Redwood City, Calif., 1990, pp. 324–325). Further, intracellular $K^+$ concentrations are maintained 20× greater than those outside of the cell. In order to maintain these gradients, many cells are required to expend between thirty and fifty percent of their ATP derived energy on active transport mechanisms (Christopher Mathews and K. E. van Holde, "BIOCHEMISTRY", Benjamin/Cummings Pub., Redwood City, Calif., 1990, pp. 324–325). It follows that any effects destroying or altering these gradients over time will eventually prove fatal to the cell.

Using oligodendroglioma hybrid cells (ROC-1), it has been shown that ATP depletion to less than 5% of the control caused a 200% increase in cell volume, bleb formation, followed immediately after by LDH release and irreversible cell death (Marianne S. Jurkowitz-Alexander, Ruth A. Altschuld, Charlene, M. Hohl, J. David Johnson, John S. McDonald, Todd D. Simmons, and Lloyd A. Horrocks, *Jnl. of Neurochemistry*, 59:1, pp. 344–352, 1992). In the same instance, it was shown that depletion to 10% of the normal ATP levels, by blocking glycolytic pathways and partially inhibiting mitochondria respiration by increased amytal concentrations, caused 50% cell death within 40 min. In a similar study (Marianne S. Jurkowitz-Alexander, Ruth A. Altschuld, Steven A. Haun, Ralph E. Stephens, and Lloyd A. Horrocks, *Jnl. of Neurochemistry*, 61:4, pp. 1581–1584, 1993), using the same modeling system, it was shown that, independently of osmotic swelling and bleb formation, ATP depletion was able to induce LDH release.

It has been widely accepted that glioblastoma (the term referring to the groups III and IV gliomas) has been shown to be producing ATP primarily through glycolytic pathways. It follows that, since the glioblastoma cells normally sustain ATP concentrations lower than in properly functioning cells, significant up regulation of ATP catabolism via $\Delta\Psi$m destabilization while simultaneously short circuiting the $H^+$ ion transport system will more significantly affect the less efficient, highly invasive, rapidly growing glioblastoma cells. Because of this difference, the effects that RIAE will have upon glioma cells, relative to normally functioning astrocytes should be, to some quantifiable amount, more toxic.

It is widely accepted that normal aerobic metabolism (employing the Kreb's cycle) is much more efficient than glycolysis alone. The glioma cells must generate ATP primarily through glycolysis. This process produces eight (8) moles ATP per mole of glucose (including the mitochondria electron transport chain). The normal astrocyte, however, is able to produce eight (8) mole's ATP per mole of glucose via glycolysis in addition to the citric acid cycle which produces 38 moles of ATP per mole of glucose (Christopher Mathews and K. E. van Holde, "BIOCHEMISTRY", Benjamin/Cummings Pub., Redwood City, Calif., 1990, pp. 449–450). Furthermore it has been found that most gliomas have a higher internal pH relative to healthy brain tissues and a lower pH may be deleterious to gliomas (Cadoux-Hudson T. A., Blackledge M. J., Rajagopalan B., Taylor D. J., Radda G. K. *Br Jnl of Cancer*, 60:3, pp. 430–436, 1989, Daly P. F. and Cohen JS, *Cancer Research*, 49, pp. 770–779, 1989, Oberhaensli RD, Bore P. J., Rampling R. P., Hilton-Jones D., Hands L. J., Radda G. K., *The Lancet*, July 5th, pp. 8–11, 1986, Rottenberg D. A., Ginos J. Z., Kearfott K. J., Junck L., Bigner D. D., *Ann. Neurol.*, 15(supplement):S98–102, 1984, and Vaupel P., Kallinowski F., Adams G. E., *Cancer Research*, 49, pp. 6449–6465, 1989). This increased pH is necessary in order to maintain the high rate of growth maintained by these cells (Johnson J. D., Epel D., Paul M., *Nature (London)*, 262, pp. 661–664, 1976, L'Allemain G., Paris S., Franchi A., Cragoe E. J. Jr., Pouyssegur J., *Jnl. of Biol. Chem.*, 259, pp. 4313–4319, 1984, Moolenaar W. H., Tertoolen L. G., De Laat S. W., *Nature (London)*, 312, pp. 371–374, 1984, Ober S. S., Pardee A. B., *Proc. Natl. Acad. Sci. (USA)*, 84, pp. 2766–2770, 1987, and Schulinder S., Rozengurt E., *Proc. Natl. Acad. Sci (USA)*, 79, pp. 7778–7782, 1982). Indeed, experiments have proven that intracellular alkalization has been shown to commit DNA into synthesis (Moolenaar W. H., Boonstra J, Van der Saag, and De Laat S. W., *Jnl. of Biochemistry*, 256, 1981). One of the mechanisms by which cells maintain this alkalinity is by activation of the Na/H antiport mechanisms (Schulinder S., Rozengurt E., *Proc. Natl. Acad. Sci. (USA)*, 79, pp. 7778–7782, 1982). This would suggest that glioma cells are maintaining a higher time averaged rate of $Na^+$ accumulation than cells functioning at lower pH values (even without RIAE agitation). This in turn would also indicate an already increased energy expenditure on $Na^+$ efflux relative to nontransformed cells, further handicapping it towards sustaining induced energy and ATP deficits. By comparison, one can say with a margin of certainty that the glioma cell is less aptly equipped to survive a prolonged duration of ATP (or energy) depletion, relative to normal glial cells.

RIAE relies upon the fact that electroporation, summarized and described immediately below, is a critical phenomena induced by non-ionizing electromagnetic radiation.

Electroporation

Electroporation is the technique by which cell membranes are induced to dissociate, either permanently or reversibly (membranes that reseal), by the generation of critical transmembrane potentials ($\Delta\Psi M$). The transmembrane potentials are generated by applying an electric field of low frequency and high field density until such time that a structural deformation of the cellular phospholipid bilayer occurs (in the subject invention the field is pulsed). It should be noted that the radiation levels required for the subject process of electroporation are significantly lower than traditional high energy radiation treatments. The deformative process is, for the most part, vectorially unidirectional until the "poration threshold" of the membrane is reached, after which the poration process begins, either irreversibly or reversibly, depending on field strength, exposure time, field pulse characteristics, and the like. The actual poration threshold is determined by the chemical composition and spatial orientation of the cell's membrane, as well as by the density of and time of exposure to the incident field. (Eberhard Neumann, Arthur E. Sowers, and Carol A. Jordan, "Electroporation and Electrofusion in Cell Biology," Plenum Publishing Company, New York, N.Y., 1989).

It must be emphasized that it is the morphological nature of the membrane and the cell's metabolic resistance that determines the critical time and field strength parameters of the lysis threshold. It is not just the potential applied to the cell, rather it is the transmembrane potential (an attenuated or amplified form of the applied field), that attains the critical threshold value for reversible or irreversible rupture.

It is important to understand the relationship between an applied field and the transmembrane field that is induced in the cell. The relationship is described or approximated by the Schwann Equation (Eberhard Neumann, Arthur E. Sowers, and Carol A. Jordan, "Electroporation and Electrofusion in Cell Biology," Plenum Publishing Company, New York, N.Y., 1989) for the spherical shell model of a cell. The geometry of the cell is simplified to two concentric spheres with a radial difference of 50 nm (the 50 nm separation approximates the thickness of the phospholipid membrane). Let $D_p$ represent the change in potential across the 50 nm membrane. Also, let I represent the internal spherical radius, E the applied field, $\omega$ the angular frequency of the field, and G the angle measured with respect to the normal of the cell membrane's surface. Letting $R_i$ represent the internal resistance, $R_e$ the external resistance, and $C_m$ the membrane capacitance.

$$D_p = (1.5[I][E]/[1+(\omega T)^2]^{0.5}) \cos G \quad (1)$$

Where T is obtained by the following:

$$T = [I][C_m][R_i+(R_e/2)] \quad (2)$$

In order to initiate the electroporative process, it has been shown that the induced transmembrane potential must lie in the range of about 0.5 V to about 0.7 V or more generally between about 0.5 V and about 1.5 V (Eberhard Neumann, Arthur E. Sowers, and Carol A. Jordan, "Electroporation and Electrofusion in Cell Biology," Plenum Publishing Company, New York, N.Y., 1989) with the lower voltage values yielding generally reversible processes of electroporation.

By generating fields to within critical time and field strength parameter's, holes can be temporarily or permanently induced in the cell's membrane. At body temperature, the kinetics for pore resealing are favorably enhanced, thus making such reversible electroporation applications more feasible. By (over time) inducing small, reversible pores in the cell membranes, one can generate temporary transmembrane ion gradient degradation over periods of one to two hours or for other times with altered conditions. As long as the applied pulse length is short enough, the induced transmembrane potential is not too high, and the interval between pulses is long enough to allow gradient normalization between successive exposures for normal cells, one can create a time averaged decrease in the transmembrane $Na^+$ gradient and a corresponding increase in the ATP consumption rates.

Assuming both normal and abnormal cells are to be present, it is expected that (over prolonged duration's of inducing transient membrane pores) there will be a time dependent decrease in cell viability. It is claimed here, that the time tolerance of some highly malignant cells, (including glioma cells) will be less than most nonmalignant cells (or astrocytes, oligodendrocytes, and the like)

It must be remembered that it may not be necessary to bring the membrane to the point of poration to induce necrosis in malignant cells. By simply increasing the transmembrane potential, one can increase the normal rate of ionic diffusion. Using the same logic as above, this too would render the glioma cells preferentially susceptible to an increased rate of ATP depletion, if the rate of ionic diffusion induced were sufficient. Indeed, we have found data that suggests that the energy consumption (here in the form of ATP) could be indirectly influenced by or triggered by, rather than directly the result of, the elevated transmembrane potential. The data presented in the Experimental section below indicates that an ion (most likely $Ca^{2+}$) oscillation can be controllably induced in cells by a particular transmembrane potential and duration. The introduction of this type of oscillation event can be controllably induced in cells via the disclosed method and thus the energy expenditure of the transformed cells can be caused to be lethal, while non-transformed cells may be able to withstand a number of these onsaults. Because $Ca^{2+}$ ratios of 20,000 to 1 are often maintained within glial cell (extra to intra cytoplasmic), a $Ca^{2+}$ increase could be a cytotoxic effector.

Especially in cases of oligodendrocytoma and astrocytoma (where many of the tumors originate in the white matter) such RIAE or nonporation increase in ionic diffusion applications may be quite useful. Due to the relatively small variety of cells and structures to be compared and contrasted with respect to their absorption of fields, the white matter provides an "arena" in which to test this and other embodiments. Axons, oligodendrocytes, and oligodendroglioma cells are sometimes the only competing structures for field absorption in this region.

For utilizing the subject method that utilizes non-ionizing radiation, a non-ionizing radiation generating means is required to produce the pulsing field within a treatment domain or zone that contains the cells to be treated. The generated pulsed radiation is at a level sufficient to create cellular transmembrane potentials ($\Delta\Psi M$) ranging from between about 0.2 V to about 1.5 V or more specifically between about 0.2 V to about 0.7 V in the susceptible malignant cells for a selected and sufficient time period to cause necrosis in the abnormal cells. As indicated above, the necrosis is via electroporation (specifically, reversible electroporation) or increases in ionic diffusion that induce lethal metabolic alterations over time.

The subject method induces necrosis in susceptible malignant cells found in a collection of cells either within tissue in general or specifically in a patient. The method positions the collection of cells within the treatment domain and the non-ionizing radiation field is pulsed with pulses having a pulse duration, interval gap between pulses, and pulse intensity selected to produce necrosis in the susceptible malignant cells by creating a transmembrane potential that causes an increase in ionic diffusion in the susceptible malignant cells or repeatedly generates reversible electroporation of the susceptible malignant cells. The increased ionic diffusion or reversible electroporation cause a lethal metabolic alteration in the susceptible malignant cells. Usually, the pulse duration, interval gap between pulses, and pulse intensity are selected to produce necrosis in the susceptible malignant cells based on cellular membrane or metabolic characteristics of the susceptible malignant cells.

To summarize the possible pathways for induction of necrosis, the subject method may function in susceptible malignant cells via creating a transmembrane potential that causes an increase in ion diffusion in the susceptible malignant cells, thereby causing a lethal metabolic alteration in the susceptible malignant cells. Also, the subject method may function in susceptible malignant cells via creating an increase in ATP usage in the susceptible malignant cells, thereby causing a lethal metabolic alteration in the susceptible malignant cells. Additionally, the subject method may function in susceptible malignant cells via creating a deleterious alteration in internal pH in the susceptible malignant cells by interfering with normal ion distributions, thereby causing a lethal metabolic alteration in the susceptible malignant cells. Further, additional reasons may exist for selective necrosis caused by the subject method.

EXPERIMENTS

Ion Oscillation in Cultured Cells

The utilized cells were from a cell culture of C6 rat brain glioma cells that were cultured in RPMI 1640, with 10% FBS, and kept in the log growth phase. In the cells own medium, and at room temperature, the cells were placed on a inverted microscope and patched using a perforated patch clamp technique (Kettenmann and Grantyn, Practical Electrophysiological Techniques, pp. 274–278, Wiley-Liss, 1992, which is herein incorporated by reference). Briefly, the technique involved incorporating the antibiotic nystatin (Sigma N5303) into the electrode buffer (Kettenmann and Grantyn, Practical Electrophysiological Techniques, pp. 274–278, Wiley-Liss, 1992). A seal between the electrode and the cell was obtained. As the antibiotic came into equilibrium over with the membrane portion within the electrode, the resistance of the membrane over the whole cell dropped. In this way the transmembrane potential could be monitored without allowing organelles to be dialyzed into the electrode, and the actual response of a cell to external stimulus could be better monitored. The cells were then exposed to a voltage of 25 microsecond duration, delivered by two stainless steel caliper electrodes mounted on a micrometer (from BTX Corporation, San Diego, Calif.), in their original media.

Figure 1:
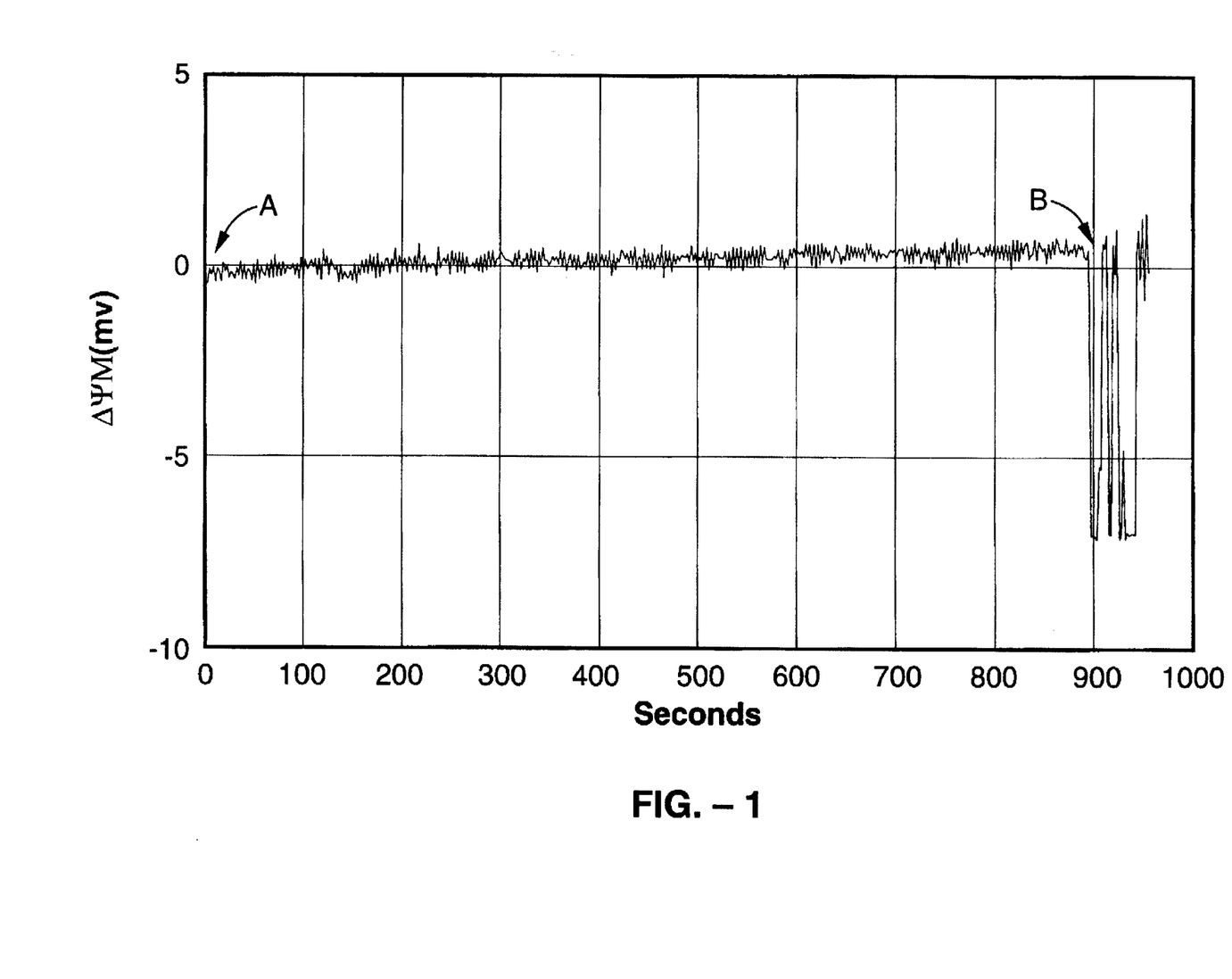
FIG. 1 is a graph of data collected for cells in which a 100 v/cm pulse was applied.
Figure 2:
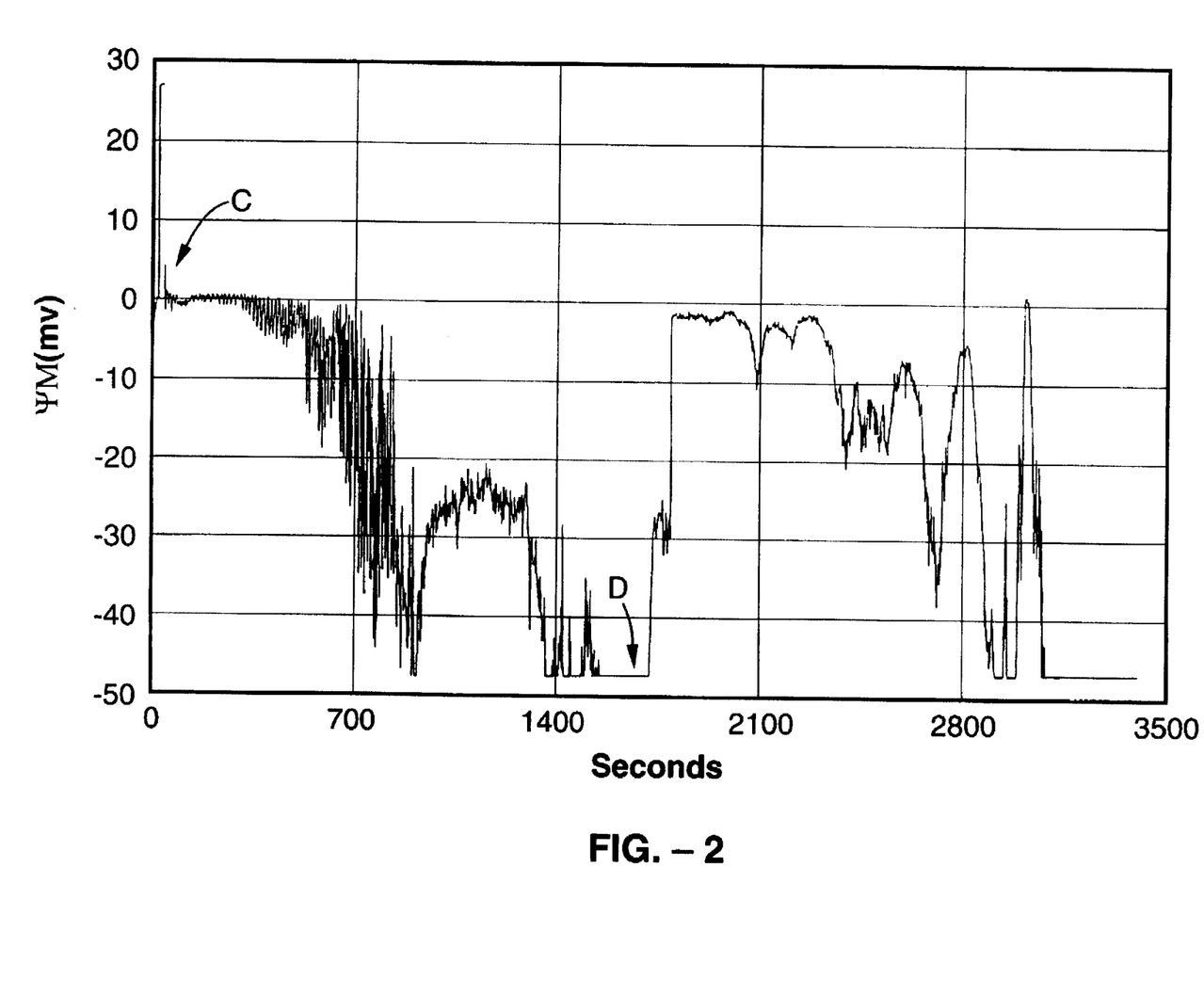
FIG. 2 is a graph of data collected for the cells used in FIG. 1 after the pulse experiment of FIG. 1 in which a first 200 v/cm pulse was applied.
Figure 3:
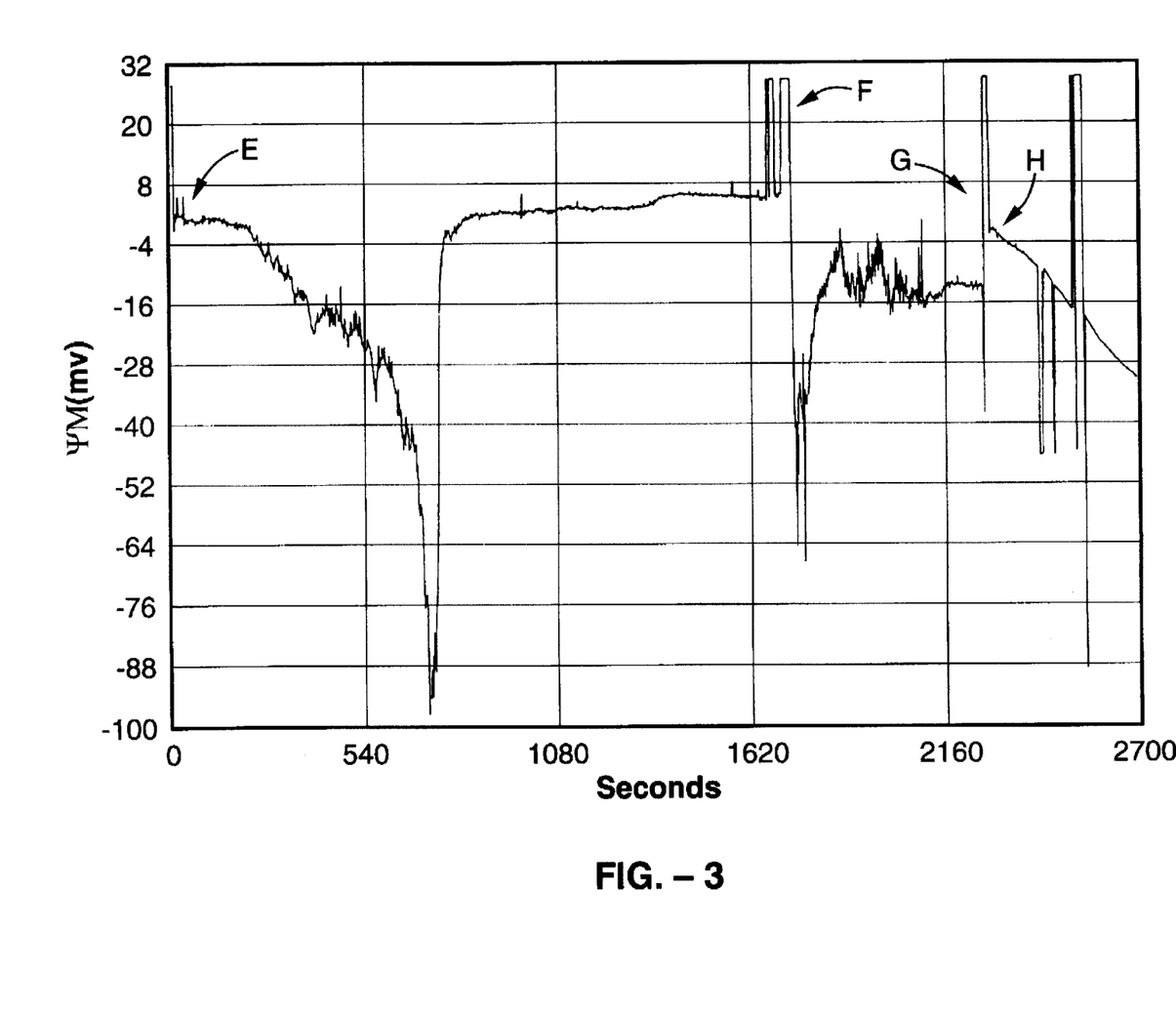
FIG. 3 is a graph of data collected for the cells of FIG. 1 after the pulse experiments of FIGS. 1 and 2 in which a second 200 v/cm pulse was applied.

Note that the same cells are used for all of the data presented in FIGS. 1–3. FIG. 1 presents the time (X axis in seconds) versus voltage (Y axis in millivolts relative to resting potential) data for the cell in which a pulse with a field strength of only 100 v/cm was made at point A (t=0). At point B, the equipment was checked, disabling the recording mechanism (an effect like that seen in FIG. 3-G below).

Presented in FIG. 2 is time versus voltage data for cells pulsed at point C. At point C the cells were exposed to a field strength of 200 v/cm (a value far less than electroporative onset) for 25 microseconds. An almost harmonic amplification was observed for a significant period of time. Then in and of its own time, the cells hyperpolarize (a process which requires a great deal of energy). In a non-stoichiastic, inverted exponential type fashion (over the scope of 10 to 15 minutes) the cells dipped down to −200 mV, relative to its resting potential. Point D indicates where the chart went off-scale (due to not expecting the noted phenomenon), but the metering devices on the amplifier in current clamp mode did indicated the −200 mV figure. Note that the cells drop quickly back to a resting state (t=182 ms) and then continue to flux. In order to ascertain if this result was an interference artifact or some other error, the cells were pulsed again, as shown in FIG. 3.

FIG. 3 exhibits data for the same cells, the same patch, and after the periods shown in FIGS. 1 and 2. Point E shown here monitoring began on the backside of a 25 microsecond pulse applied at t=0. The pulse (same size as previously utilized) stabilized the cell for a lag time similar to that in FIG. 1, after pulsation. Note how the exponential dive to −100 mV is of approximately the same form as that of FIG. 2. To ensure authenticity of the results, at point F we applied three pulses of 960 volts/cm to produce known electroportation (note that the signal recorder was turned off during the actual pulse exposure). After these three pulses we saw a gradual decrease in the potential, which was restored and began to oscillate (a sign of a dying cell). Point G is where additional configuration values for the apparatus were checked (these were initially unable to be monitored with the utilized recorder configuration) to further reduce error possibilities. At point H the membranes in contact with the electrode was ripped away from the cells to assure that these readings were not artifacts.

Intended Experiments

A) The first (#1) of 21 batches of cells (normal fetal rat glial cells in primary culture) will be placed in a temperature controlled electroporation chamber.

B) The cells (normal fetal rat glial cells in primary culture) will be exposed to an electric field consisting of five (5) pulses at a duration of one (1) microsecond per pulse. The voltage will be determined by the average cell's size, so as to produce about 0.2 V to about 0.7 V for the transmembrane potentials.

C) The second (#2) batch will be exposed to the same conditions, however the exposure time will be increased to 10 microseconds. Each batch thereafter will be exposed to an identical field strength, varying the integral of the exposure time (T) by the relationship:

$T=5(N)$ (where N=batch number)

D) After each exposure, the cell's ability to survive (or the cell's viability) will be assayed. This assay will be done using various techniques. After exposure, Trypan Blue can be added directly to the electroporation medium to test for membrane impermeability. Cell platting efficiency can be tested, after the cells have been washed, resuspended, and incubated for 24–48 hours. Further methods are commercially available Life and Death kit's (available from Polysciences, Inc. 400 Valley Road, Warrington, Pa. 18976 and involves hydroethidine which enters and stain living cells without cellular trauma), as well as LDH assays, and uptake kinetics measurement. The method which produces the most similar results (100% viability) for the non exposed cells in electropotation medium, and the same cells in their normal culturing medium (the controls), will be employed.

E) The cell's viability versus the time integral of exposure will be obtained, and plotted.

F) After graphical analyses, the point at which the cells viability level approaches zero will be marked.

G) Another series of 21 batches, of the same cells (normal fetal rat glial cells in primary culture), will be performed. Maintaining this total time integral, the exposure times will be separated by (in our case) five (5) seconds. Batch #1 will receive the total terminal integral (TTI) of exposure as the batch, in the first series from which the marked ZERO (0) VIABILITY point will be determined. Then the following (Batch #2) will receive an exposure of TTI/2, followed by a pause of five (5) seconds, then exposed again to TTI/2. Each time the TTI is resolved, a non pulse time of five (5) seconds will separate the pulse applications. Each additional exposure time will be executed according to the following relationship:

The pulse time (PT) for batch #N
$PT=TTI/N$

The total non-pulsed time (NPT):
$NPT=5(N-1)$

H) In this way, we will determine the point at which the cells are able to maintain viability, despite intermittent reversible electroporation. The sequence at which the cells are able to maintain a majority of their viability (relative to controls) will be obtained.

I) We shall then further resolve the pulse intermittence and pulse duration's.

J) Next, we will run an identical trial on the glioma cells, which will be selected for being of similar size to the non-malignant line of fetal rat glial cells in primary culture.

K) After collecting the data from the first series in both the glioma and glial cells, we will plot the data with various standard techniques. This alone may establish that the transformed cells' ability to cope with the effects of increased membrane permeability are less than those of the normal cells.

L) After running the second series of the above mentioned protocol on the transformed cells, we will be able to verify the preferential vulnerability of malignant cells (in this case of rat glioma cells) by means of their inability to cope with intermittent exposures to electroporation. Then, using the aforementioned data, we will use a genetically marked form of the cancer cells (i.e., IacZ transfected C6 or RG2 cells which express a protein which fluoresces upon excitation so as to distinguish cancer from primary (non-cancer) cells) which express visible markers. Mixing the cancer cells with the primary cells, we will expose the mixture to pulse values and intermittentcies obtained above, trying to target only the cancer cells. The above (and below) procedures will be tested for many forms, both human and animal, cancer cell forms. If positive results are obtained in vitro, the above principles will be tested in vivo using a living rat (or similar animal) model in a similar manner as that described in the following publication (which is herein incorporated by reference): Salford et al., BBRC, Jul. 30, 1993, 194(2) :938–943.

In the case that the conductivity of the cells' surrounding medium is too high to allow proper field generation without joule heating, we will use a coil configuration to induce a focused magnetic field, thereby inducing a relatively generated electric field, independent of the cells' surrounding conductivity. It is ultimately this method that will be used in vivo.

Electric Field Generation Techniques

Usually, the non-ionizing and pulsed radiation is generated between opposing plates or opposing poles. In the pulsed field apparatus, the non-ionizing radiation is generated at a level sufficient to induce a $\Delta\Psi M$ of about 0.2 V and about 1.5 V or more specifically from about 0.2 V to about 0.7 V in the exposed cells for a sufficient time period to cause necrosis in the cells via the reversible electroporation.

One manner to generate an initial non-ionizing electric field is to utilize an ECM 200 electric cell manipulator (available from BTX, San Diego, Calif.) attached to a glass slide exposure chamber (a suitably modified BTX 450-1, from BTX, San Diego, Calif.). The voltage generated will be monitored by an IMTEC digital oscilloscope (Capax Inst., Gothenburg, Sweden).

Further in depth, the non-ionizing and pulsed radiation (the electric field) will be generated differently, depending on the conductive nature of the system. If the system consists of cells (in vitro) suspended in, for example, 0.3M mannitol, glucose, sucrose, or any other noncharged sugar or compound, the fields should be generated using conventional techniques. In particular, the cells are placed onto a glass slide and in between two metal electrodes. In this instance, the conductivity of the liquid surrounding the cells is low enough that the applied voltage (applied over the electrodes) will result in an electric field approximating the value: $E=v/d$ where $v=$voltage and $d=$distance between the electrodes. The field will be induced such that the $\Delta\Psi m$ attains a value in the range of about 0.2 to 1.5V, depending upon the aspect of RIAE being tested and according to equation #1.

If the conductivity of the solution surrounding the cells is too high, and the application is to cells in suspension, the voltage will be generated relativistically. In order to test RIAE, which is dependent upon the cell's metabolic resistance in its normal extracellular media and corresponding pI, we will ultimately use an electric field generated by a B (magnetic) field. In vitro a simple approach is used consisting of a coil with extremely low resistance and high surface area, and a high frequency, voltage generator.

In the case where the cells are in vivo, one approach similar to, but not identical with, the processes used in brain stimulation will be used. (Davey et al., IEEE Transactions on Biomedical Engineering, Vol. 38, No. 5, May 1991). The difference being that the resultant E field generated will be at a much higher value and frequency than those used in neuro stimulation.

It is noted that one possible reason why the subject method (using high frequency E fields) has not been attempted is as follows. Most researchers have referenced the Schwann equation extensively when discussing the $\Delta\Psi m$ produced by the E field. In order to focus (relativistically) an E field, one must use high frequencies, higher than those typically employed in electroporation. According to the Schwann equation (1) (where $\omega=2\pi f$, and $f=$frequency of the field) the $\Delta\Psi m$ will drop off as $\omega \rightarrow \infty$. In estimation, one would expect the cell's membrane tolerance to an applied field to be inversely correlated to the generated $\Delta\Psi m$. So, if we assume that assumption holds, frequencies in the MHz range, would have little, if any, effect in the way of electroporation. This is, however, not the case since the Schwann equation has been found to be true only in the lower frequencies.

It should also be noted that it may be possible to test RIAE effects at $\Delta\Psi m$ values between 0.2 and 0.7V (or between the wider range of about 0.2 to 1.5V) using more conventional techniques. (see, Salford et al. above).

It is important to note that RIAE will, in a controlled manner, destroy most transmembrane ionic gradients. Since the proton pump and $Na^+/K^+$ pump are the primary functioning entities which generate this in equilibrium, dystrophy of the gradients will concomitantly increase ATP uptake. At the same time, glucose intake (in many cells) will be reduced. Since (in the case of oligodendroglioma) the invasive cells are already less efficient in their energy production in the form of ATP, their ability to recover from long durations of transmembrane ionic gradient assault should be significantly less than normal, properly functioning cells.

It is stressed that the references cited above in this disclosure are to provide those skilled in the art with a quick citation source of relevant information and techniques and are incorporated herein by reference.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. A method for inducing necrosis in susceptible malignant cells, comprising the steps:
   a) positioning a collection of cells containing the susceptible malignant cells within a treatment domain;
   b) subjecting said treatment domain to a non-ionizing radiation field;
   c) pulsing said non-ionizing radiation field with a frequency and an intensity selected to produce necrosis in the susceptible malignant cells; and
   d) creating by said pulsing a transmembrane potential that causes an increase in ionic diffusion in the susceptible malignant cells or generates reversible electroporation of the susceptible malignant cells.

2. A method for inducing necrosis in susceptible malignant cells, according to claim 1, wherein said pulsing frequency and intensity are selected to produce necrosis in the susceptible malignant cells based on cellular membrane characteristics of the susceptible malignant cells.

3. A method for inducing necrosis in susceptible malignant cells, according to claim 1, wherein said created transmembrane potential is about 0.2 V to about 1.5 V.

4. A method for inducing necrosis in susceptible malignant cells, according to claim 1, wherein said created transmembrane potential is about 0.2 V to about 0.7 V.

5. A method for inducing necrosis in susceptible malignant cells, according to claim 1, wherein said induced necrosis in the susceptible malignant cells is caused by said increase in ionic diffusion.

6. A method for inducing necrosis in susceptible malignant cells, according to claim 1, wherein the induced necrosis in the susceptible malignant cells is generated by said reversible electropotation.

7. A method for inducing necrosis in susceptible malignant cells, according to claim 1, further comprising the step of causing, from said created transmembrane potential, an oscillation in calcium, sodium, or potassium ion concentration in the susceptible malignant cells, thereby causing a lethal metabolic alteration in the susceptible malignant cells.

8. A method for inducing necrosis in susceptible malignant cells, according to claim 1, further comprising the step of causing, from said created transmembrane potential, an increase in ATP usage in the susceptible malignant cells, thereby causing a lethal metabolic alteration in the susceptible malignant cells.

9. A method for inducing necrosis in susceptible malignant cells, according to claim 1, further comprising the step of causing, from said created transmembrane potential, a deleterious internal pH in the susceptible malignant cells, thereby causing a lethal metabolic alteration in the susceptible malignant cells.

10. A method for inducing necrosis in susceptible malignant cells, comprising the steps:
   a) positioning a collection of cells containing the susceptible malignant cells within a treatment domain;
   b) subjecting said treatment domain to a non-ionizing radiation field;
   c) pulsing said non-ionizing radiation field with pulses having a pulse duration, interval gap between pulses, and pulse intensity selected to produce necrosis in the susceptible malignant cells; and
   d) creating by said pulsing a transmembrane potential that causes an increase in ionic diffusion in the susceptible malignant cells or generates reversible electroporation of the susceptible malignant cells, thereby causing a lethal metabolic alteration in the susceptible malignant cells.

11. A method for inducing necrosis in susceptible malignant cells, according to claim 10, wherein said pulse duration, interval gap between pulses, and pulse intensity are selected to produce necrosis in the susceptible malignant cells based on cellular membrane characteristics of the susceptible malignant cells.

12. A method for inducing necrosis in susceptible malignant cells, according to claim 10, wherein said created transmembrane potential is about 0.2 V to about 1.5 V.

13. A method for inducing necrosis in susceptible malignant cells, according to claim 10, wherein said created transmembrane potential is about 0.2 V to about 0.7 V.

14. A method for inducing necrosis in susceptible malignant cells, according to claim 10, wherein said lethal metabolic alteration in the susceptible malignant cells is caused by said increase in ionic diffusion.

15. A method for inducing necrosis in susceptible malignant cells, according to claim 10, wherein said lethal metabolic alteration in the susceptible malignant cells is generated by said reversible electroporation.

16. A method for inducing necrosis in susceptible malignant cells, according to claim 10, further comprising the step of causing, from said created transmembrane potential, an oscillation in calcium, sodium, or potassium ion concentration in the susceptible malignant cells, thereby causing a lethal metabolic alteration in the susceptible malignant cells.

17. A method for inducing necrosis in susceptible malignant cells, according to claim 10, further comprising the step of causing, from said created transmembrane potential, an increase in ATP usage in the susceptible malignant cells, thereby causing a lethal metabolic alteration in the susceptible malignant cells.

18. A method for inducing necrosis in susceptible malignant cells, according to claim 10, further comprising the step of causing, from said created transmembrane potential, a deleterious alteration in internal pH in the susceptible malignant cells, thereby causing a lethal metabolic alteration in the susceptible malignant cells.

19. A method for treating a patient having malignant cells, wherein the treatment induces necrosis in the malignant cells that are susceptible to said treatment, comprising the steps:
   a) selecting the patient with the malignant cells that are susceptible to the treatment because the susceptible malignant cells produce ATP primarily through glycolytic pathways or the susceptible malignant cells have a variant ion gradient relative to nonsusceptible healthy cells;
   b) positioning the patient to place the susceptible malignant cells within a treatment domain;
   c) subjecting said treatment domain to a non-ionizing radiation field; and
   d) pulsing said non-ionizing radiation field with pulses having a pulse duration, interval gap between pulses, and pulse intensity selected to produce necrosis in the susceptible malignant cells by creating a transmembrane potential that causes an increase in ionic diffusion in the susceptible malignant cells or generates reversible electroporation of the susceptible malignant cells, thereby causing a lethal metabolic alteration in the susceptible malignant cells.

20. A method for inducing necrosis in susceptible malignant cells, according to claim 19, wherein said created transmembrane potential is about 0.2 V to about 1.5 V.

21. A method for inducing necrosis in susceptible malignant cells, according to claim 19, wherein said created transmembrane potential is about 0.2 V to about 0.7 V.

22. A method for inducing necrosis in susceptible malignant cells, according to claim 19, wherein said lethal metabolic alteration in the susceptible malignant cells is caused by said increase in ionic diffusion.

23. A method for inducing necrosis in susceptible malignant cells, according to claim 19, wherein said lethal metabolic alteration in the susceptible malignant cells is generated by said reversible electropotation.

24. A method for inducing necrosis in susceptible malignant cells, according to claim 19, further comprising the step of causing, from said created transmembrane potential, an oscillation in calcium, sodium, or potassium ion concentration in the susceptible malignant cells, thereby causing a lethal metabolic alteration in the susceptible malignant cells.

25. A method for inducing necrosis in susceptible malignant cells, according to claim 19, further comprising the step of causing, from said created transmembrane potential, an increase in ATP usage in the susceptible malignant cells, thereby causing a lethal metabolic alteration in the susceptible malignant cells.

26. A method for inducing necrosis in susceptible malignant cells, according to claim 19, further comprising the step of causing, from said created transmembrane potential, a deleterious alteration in internal pH in the susceptible malignant cells, thereby causing a lethal metabolic alteration in the susceptible malignant cells.

* * * * *